United States Patent [19]

Kottemann

[11] Patent Number: 4,659,310
[45] Date of Patent: * Apr. 21, 1987

[54] ORTHODONTIC ARCHWIRE

[76] Inventor: William J. Kottemann, 755 Tonkawa Rd., Long Lake, Minn. 55356

[*] Notice: The portion of the term of this patent subsequent to Apr. 29, 2003 has been disclaimed.

[21] Appl. No.: 797,443

[22] Filed: Nov. 13, 1985

Related U.S. Application Data

[63] Continuation-in-part of Ser. No. 693,381, Jan. 22, 1985, Pat. No. 4,585,414, which is a continuation-in-part of Ser. No. 501,482, Jun. 6, 1983, abandoned.

[51] Int. Cl.⁴ ................................................ A61C 3/00
[52] U.S. Cl. ...................................................... 433/20
[58] Field of Search ........................... 433/20; 528/391

[56] References Cited

U.S. PATENT DOCUMENTS

| Re. 30,332 | 7/1980 | Wallshein | 433/20 |
| Re. 30,593 | 4/1981 | Wallshein | 433/20 |
| 3,504,438 | 4/1970 | Wittman et al. | 433/20 |
| 3,563,961 | 2/1971 | Pickle et al. | 528/391 |
| 3,773,720 | 11/1973 | Vogel | 528/391 |
| 3,988,832 | 11/1976 | Wallshein | 433/21 |
| 4,024,119 | 5/1977 | Sonnenberg | 528/391 |
| 4,037,324 | 7/1977 | Andreasen | 433/20 |
| 4,050,156 | 9/1977 | Chasanoff et al. | 433/20 |
| 4,127,713 | 11/1978 | Campbell | 528/391 |

Primary Examiner—John J. Wilson
Attorney, Agent, or Firm—Lloyd L. Zickert

[57] ABSTRACT

An article of manufacture for use in orthodontic procedures, comprising an extruded plastic rod reinforced with a stainless steel wire core. The article is found to exhibit substantially greater flexibility and resiliency than a stainless steel wire of the same outside dimension.

7 Claims, 8 Drawing Figures

ORTHODONTIC ARCHWIRE

DESCRIPTION

The present application is a continuation-in-part of my copending application Ser. No. 693,381, filed Jan. 22, 1985, now U.S. Pat. No. 4,585,414 entitled "Orthodontic Arch Wire", which is a continuation-in-part of my application Ser. No. 501,482, filed June 6, 1983, entitled "Orthodontic Wire", now abandoned.

This invention relates generally to orthodontic appliances, and more specifically to a new article of manufacture useful in the correction of maloccluded teeth, and still more specifically to an improved orthodontic archwire.

BACKGROUND OF THE INVENTION

In the correction of alignment and positioning of maloccluded teeth, various mechanical arrangements are used for applying steady forces to the teeth over a prolonged period of time such that the teeth are urged into an aligned disposition within the oral cavity. Typically, brackets are fastened to certain teeth and then a wire arrangement, referred to as an archwire, is fastened to the brackets to apply forces in appropriate directions so as to urge the affected teeth into a different positional orientation. The archwire is commonly drawn from stainless steel, and it is important that it possess properties of flexibility so that it can be bent into a desired shape, while at the same time exhibiting sufficient stiffness and resiliency (inherent memory property) such that desired forces are imparted upon the teeth to be repositioned.

In the past, orthodontists have primarily employed solid or stranded stainless steel or metal alloy wires having either a circular or rectangular cross section in fabricating orthodontic archwires. The word rectangular as used herein also includes a square cross section. While stainless steel archwires of a given diameter, i.e., typically in the range of 0.016 to 0.022 inches, and rectangular archwires of various sizes, are commonly employed, they suffer from a lack of flexibility because the outside diameter is necessary to ensure that the wire will have the requisite resiliency to provide the desired forces upon the teeth. While reducing the diameter may render the wire more flexible, its resiliency is correspondingly reduced such that the wire is subject to permanent deformation and/or breakage. More recently, an archwire formed from a nickel titanium alloy and sold under the trademark "Nitinol Activ-Arch" by the Unitek Corporation of Monrovia, Calif., has been introduced which posseses the desirable characteristics of reduced stiffness (greater flexibility) and high resistance to deformation as compared to stainless steel archwire of comparable dimensions. The use of archwires of Nitinol alloy in orthodontia is described in U.S. Pat. No. 4,037,324.

In addition, orthodontic work is frequently performed on patients who may be somewhat self-conscious over their appearance and are, at times, embarrassed by the presence of the orthodontic appliances of their teeth. Stainless steel wires of a requisite diameter tend to be somewhat unsightly. U.S. Pat. No. 4,050,156 suggests coating a stainless archwire with a plastic matrix in which a suitable colorant is intermixed so as to match the natural tooth color of the patient. Here, however, the plastic material is not used as a structural member as in the present invention, but is only used as a method of applying a colorant to a stainless steel surface.

SUMMARY OF THE INVENTION

In accordance with the present invention, there is provided a dental archwire comprising an extruded, flexible plastic rod of polysulfone or Ultem reinforced with a stainless steel wire so that the composite article exhibits a total outside dimension no greater than that of prior art metal orthodontic archwires. Ultem, a polyetherimide resin, is a registered trademark of General Electric Company. The article of manufacture exhibits properties of flexibility and resiliency significantly greater than that of the prior art metal archwires. It is also found that the steel reinforced plastic rod of the present invention possesses characteristics superior to Nitinol archwire as far as its resistance to deformation is concerned. It is also less brittle and does not break as readily as Nitinol wire. The article can be easily shaped while remaining effective for its intended purpose.

While the plastic is generally clear, if desired, it may be impregnated with suitable colorants and the resulting article can thereby be rendered tooth colored so as to make it less obtrusive, but this is only a secondary advantage, the primary one being its improved flexibility and high mechanical memory property.

The dental archwire of the present invention may conveniently be produced in a co-extrusion process wherein the wire is drawn through the extruder during the polysulfone or Ultem plastic extrusion process. The stainless steel wire is found to adhere well to the plastic and will accommodate bending. Polysulfone and Ultem plastic materials are found not to leech or to absorb water and are stable at body temperatures. They are also highly abrasion resistant and, as such, possess requisite physical properties making them highly suitable as a coating or covering for metallic wires used in orthodontic procedures.

Accordingly, it is a principal object of the present invention to provide a new and improved article of manufacture useful in the field of orthodontia.

Another object of the invention is to provide an orthodontic archwire in which a stainless steel reinforcing strand is placed within a body of polysulfone or Ultem plastic material.

Another object of the invention is to provide an improved dental archwire having an outer dimension which is no greater than commonly used stainless steel or Nitinol dental archwires, but which possesses greater flexibility and increased resiliency.

Other objects, features and advantages of the invention will be apparent from the following detailed disclosure, taken in conjunction with the accompanying sheets of drawings, wherein like reference numerals refer to like parts, in which:

DESCRIPTION OF THE INVENTION

Figure 1:
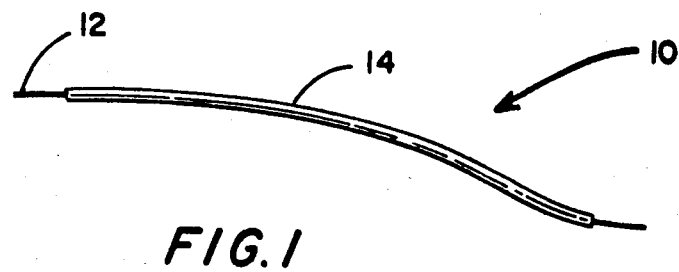
FIG. 1 is a perspective view of the article of manufcture comprising the present invention.
Figure 3:
FIG. 3 is a cross-sectional view of an alternative embodiment.

The orthodontic archwire of the present invention in one embodiment comprises an elongated, wire-reinforced round plastic rod which is indicated generally in FIG. 1 by the numeral 10. This archwire includes a round in cross section central wire core 12, which serves as a reinforcing strand for the plastic body 14. As seen in FIG. 3, the wire core may be rectangular in cross section as indicated at 12'. This core is provided with a rectangular plastic body 14'. The rectangular archwire of FIG. 3 may also be provided with a round wire core. The core wire is preferably formed from stainless steel and, in the case of the round configuration, preferably has a diameter in the range of from 0.008 inches to 0.014 inches. With the rectangular cross section, the dimensions may be in the range of from 0.010 inches×0.016 inches or 0.012 inches×0.018 inches.

Figure 2:
FIG. 2 is a cross-sectional view thereof.
Figure 4:
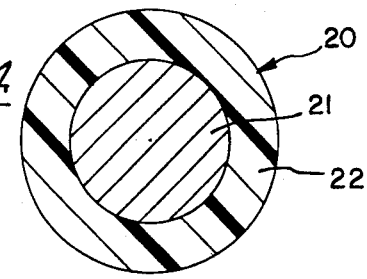
FIG. 4 is an enlarged cross-sectional view of a round archwire with a round core similar to FIG. 2 but differing in the relative dimensional relationship between the archwire and the core.

Another form of the invention is illustrated in FIG. 4 wherein the archwire, generally designated by the numeral 20, is round in cross section and includes a round in cross section metal core 21 reinforcing the plastic body 22. This embodiment differs from the embodiment in FIGS. 1 and 2 in that the round core is proportionally larger to the archwire. It will be appreciated that the metal core 21 may be of a suitable stainless steel or nickel titanium alloy or other suitable metal having a desired resiliency and that the plastic body 22 will be of a polysulfone or polyetherimide resin or any other suitable plastic resin. This figure illustrates the proportions of an archwire where the total cross-sectional dimension would be about 0.018 inches and the cross-sectional dimension of the core would be about 0.011 inches.

Figure 5:
FIG. 5 is a somewhat enlarged perspective view of a rectangular archwire having a round core.
Figure 6:
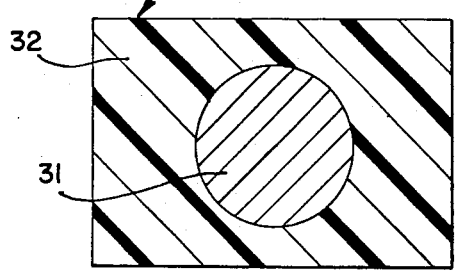
FIG. 6 is a greatly enlarged cross-sectional view of a rectangular archwire with a round core.

The rectangular archwire with round core embodiment of the invention is illustrated in FIG. 5 where it is generally designated by the numeral 30 and where the outer dimension is rectangular and the metal core is round in cross section. The metal core, designated by the numeral 31, is co-extruded with the plastic body 32. A cross-sectional view of this archwire is shown in FIG. 6 and illustrates the relative proportions of the total cross-sectional area and the round core wherein the archwire external dimension will be on the order of 0.017×0.025 inches and the round core will be on the order of 0.011 inches. It will be appreciated that the round metal core comprises about 22 percent of the total cross-sectional area, while the metal core 21 of the archwire 20 shown in FIG. 4 comprises about 37 percent of the total cross-sectional area of the archwire. In both embodiments, the core cross-sectional area represents less than fifty percent of the overall cross-sectional area of the archwire.

Figure 7:
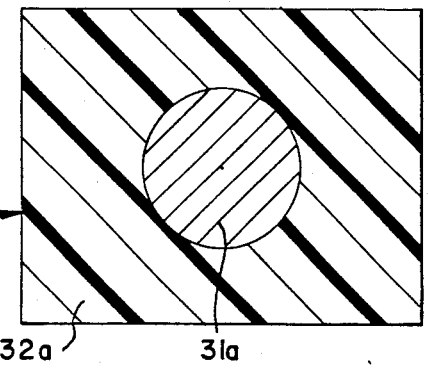
FIG. 7 is a cross-sectional view of an archwire like that in FIG. 6 except that the outer dimension of the archwire is larger.

The embodiment illustrated in FIG. 7 and generally indicated by the numeral 30A differs from that in FIG. 6 in that it illustrates a plastic archwire where the outer dimensions of the plastic body 32a are on the order of 0.022×0.028 inches, while the round metal core 31a is on the order of 0.011 inches like that in FIG. 6. The cross-sectional area of the metal core is, of course, less than half of the total cross-sectional area of the archwire.

Figure 8:
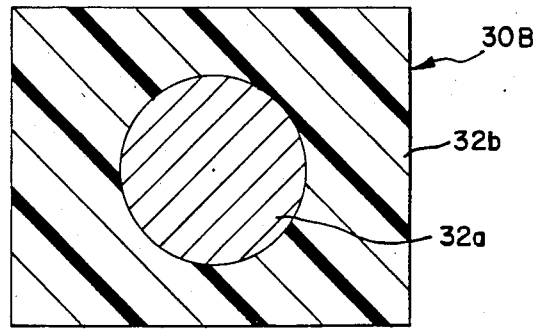
FIG. 8 is a cross-sectional view of an archwire like that in FIG. 7 having the same outer dimension but having a larger round core.

An archwire of still different dimensions is shown in FIG. 8 and generally designated by the numeral 30B wherein the outer dimensions of the plastic body 32b are of the order of 0.022×0.028 inches as in the embodiment of FIG. 7 but where the round metal core 32a is on the order of 0.013 inches. It will be appreciated that this archwire will have a lower resiliency than that of FIG. 7 by virtue of the larger core wire while maintaining the same exterior dimensions. The cross-sectional area of the core is also less than fifty percent of the overall cross-sectional area of the archwire.

As those skilled in the art are aware, stainless steel has long been used in fabricating orthodontic archwires. To provide the necessary stiffness for applying physiological biasing forces to the teeth, in the past it has been required that such stainless steel wire have a diameter of approximately 0.016–0.022 inches. As is explained in the aforementioned U.S. Pat. No. 4,037,324, wires of this dimension lack flexibility needed to bend and shape them so as to conform to the orthodontic brackets to which the archwires are intended to connect. This has made it somewhat difficult to fabricate the dental arch in situ. Additionally, this lack of flexibility limits the working range and, therefore, working time of the wire.

As was indicated in the introductory portion of this specification, I have found that, by using polysulfone resin or a polyetherimide resin material, the latter being manufactured and sold by the General Electric Company under the trademark "ULTEM", and co-extruding same with a stainless steel strand of a lesser diameter so that the resulting product has an outside diameter in the range of from 0.016 inches to 0.022 inches, the resulting stainless steel reinforced plastic rod archwire product possesses the desired flexibility property allowing it to be easily formed and bent, and providing an increase in resiliency, which is the property that affords the biasing force on teeth.

Tests conducted by an independent testing laboratory have shown that for archwires of identical cross-sectional dimensions, my archwire, in rectangular form with a round core, for which I have adopted the trademark "Filaflex", is about twenty-nine times more flexible than commercially available stainless steel archwires and about seven times more flexible than archwires fabricated from the Nitinol alloy. This test data was obtained by clamping the rectangular cross-section type archwires to a flat surface with a predetermined length of each extending beyond the edge of that surface. In each case, the wide dimension was positioned vertically and the narrow dimension horizontally. Identical loads were then applied to each sample at a point one inch out from the fulcrum (edge) and the following table shows the load required to yield the indicated deflections for each of the three samples:

|  | Load at Deflection (Pounds) | | | | | |
| --- | --- | --- | --- | --- | --- | --- |
|  | 0.1" | 0.2" | 0.3" | 0.4" | 0.5" | 0.6" |
| Maxillary ™ 18-8 Stainless Steel (.017 × 0.25) | 0.102 | 0.195 | 0.273 | 0.327 | 0.357 | 0.357 |
| Nitinol ™ Ni Ti alloy (0.017 × 0.25) | 0.036 | 0.059 | 0.071 | 0.083 | 0.089 | 0.092 |
| Filaflex ™ Polysulfone (.017 × .025) | 0.002 | 0.005 | 0.008 | 0.011 | * | * |

|  | Load at Deflection (Pounds) | | | | | |
| --- | --- | --- | --- | --- | --- | --- |
|  | 0.1" | 0.2" | 0.3" | 0.4" | 0.5" | 0.6" |
| with .009 stainless steel round core | | | | | | |

*Force caused bending to the point where cantilevered tip slipped off the fixture.

Thus, it has been determined by load testing that the article of manufacture of the present invention wherein the core wire 12 or 12' is reduced in cross section so as to lie in the above-described range of cross sections and then the polysulfone or Ultem plastic is co-extruded to be of a thickness so that the composite article has an outside dimension no greater than the cross section of the prior art Maxillary stainless steel wire and the Nitinol alloy wire alone, the article of the present invention (Filaflex) exhibits at least twenty-nine times the flexibility of the prior art solid stainless steel wire and at least seven times more flexibility than the Nitinol sample while yielding reduced biasing forces on the teeth at 0.4 inches of deflection. This reduction in force is advantageous in orthodontic work where low but steady biasing forces are deemed more efficacious than higher forces which often result in discomfort and tooth deterioration. It is also advantageous to overcome crowded teeth conditions.

The properties of polysulfone and Ultem polyetherimide resin that make them highly suitable for use in conjunction with dental archwires are that they have been certified for contact with blood and other body components, meeting U.S.P. XIX, Class VI Requirements; they have a resistance to autoclave sterilization, as well as to other methods; and they comply with F.D.A. regulations for repeated use in contact with food. Polysulfone and Ultem polyetherimide resin both have a high resistance to acids, alkalis and salt solutions. Also, they are highly stable materials so that environmental variations, such as temperature change or water immersion, result in exceptionally small dimensional changes.

In that colorants may be added to the polysulfone or Ultem polymers prior to their extrusion and orientation without detracting from their physical properties, it is possible to go from a transparent clear color to one that will match the color of teeth, making the resulting dental arch less noticeable than it is when shiny stainless steel is employed. When used with tooth colored plastic brackets, the entire system is aesthetically desired as being barely noticeable. However, the archwire of the invention can also be used with metal brackets.

The inherent hardness of both polysulfone and the Ultem resin allows them to withstand the chewing forces and other orthodontic forces within the mouth. Being abrasion resistant, they are less subject to rupture during installation or thereafter. No other plastics of which I am aware meet these criteria.

It has been found that the Filaflex plastic archwire of the present invention is not as subject to permanent deformation as is stainless steel and, hence, its ability to impose biasing forces on the teeth after being bent and/or twisted is not impaired. Furthermore, whereas the use of 18-8 stainless steel required a treatment modality in which every few weeks it would become necessary to replace a given archwire with one of successively increasing cross-sectional size, the use of the archwire made in accordance with the present invention significantly reduces the frequency with which the archwire needs replacing. During the initial stages of treatment where the teeth may be badly maloccluded, the flexibility of my archwire allows it to be bent and formed so as to reach those teeth that deviate most radically from the desired alignment and the memory properties of my wire will exert a low, steady force on the affected tooth (teeth) until it is brought into substantial alignment with neighboring teeth.

It will be understood that modifications and variations may be effected without departing from the scope of the novel concepts of the present invention, but it is understood that this application is to be limited only by the scope of the appended claims.

The invention is hereby claimed as follows:

1. In an orthodontic system for imparting corrective forces to teeth which includes appliances mounted on the teeth and an archwire connected to said appliances, the improvement being in the archwire which comprises an extruded plastic body of rectangular cross section fitting and coacting with the appliances to apply forces thereto, and a round in cross section solid reinforcing metal core wire disposed centrally within and along the longitudinal axis of said body, the cross sectional area of said core wire being less than half of the total cross sectional area of said archwire, whereby the force capability of said archwire is substantially less than that of a metal archwire of the same total cross sectional area.

2. The archwire of claim 1, wherein the plastic body is of polysulfone resin.

3. The archwire of claim 1, wherein the plastic body is of polyetherimide resin.

4. The archwire of claim 1, wherein the archwire exhibits a flexibility many times greater than nickel titanium alloy archwire of the same cross section.

5. In an orthodontic system for imparting corrective forces to teeth which includes appliances mounted on the teeth and an archwire connected to said appliances, the improvement being in the archwire which comprises a plastic body of rectangular cross section fitting and coacting with the appliances to apply forces thereto, and a round in cross section solid reinforcing metal core wire disposed centrally within and along the longitudinal axis of said body, the cross sectional area of said core wire being about 25 percent of the total cross sectional area of said archwire, whereby the force capability of said archwire is substantially less than that of a metal archwire of the same total cross sectional area.

6. The archwire of claim 5, wherein the plastic body is of polyetherimide resin.

7. The archwire of claim 5, wherein the archwire exhibits a flexibility many times greater than nickel titanium alloy archwire of the same cross section.

* * * * *